United States Patent [19]

Grupp et al.

[11] Patent Number: 5,145,864

[45] Date of Patent: Sep. 8, 1992

[54] REDUCTION OF VOLUNTARY ALCOHOL CONSUMPTION BY TREATMENT WITH ANGIOTENSIN CONVERTING ENZYME INHIBITORS

[75] Inventors: Larry A. Grupp, Downsview; Edward Perlanski, Burlington; Robert B. Stewart, Toronto, all of Canada

[73] Assignee: Alcoholism and Drug Addiction Research Foundation, Toronto, Canada

[21] Appl. No.: 96,951

[22] Filed: Sep. 15, 1987

[51] Int. Cl.⁵ .................. A01N 43/36; A61K 31/40
[52] U.S. Cl. ................................. 514/423; 514/811
[58] Field of Search ............ 514/408, 423, 415, 811, 514/359; 424/94.1, 94.2

[56] References Cited

U.S. PATENT DOCUMENTS

| | | | |
|---|---|---|---|
| 4,470,988 | 9/1984 | Watthey | 424/263 |
| 4,474,778 | 10/1984 | Gordon et al. | 424/244 |
| 4,656,188 | 4/1987 | Veber et al. | 514/423 |
| 4,785,089 | 11/1988 | Blaser et al. | 540/523 |
| 4,816,466 | 3/1989 | Sugihara et al. | 314/319 |
| 4,871,842 | 10/1989 | Sugihara et al. | 540/523 |

OTHER PUBLICATIONS

Grupp, L. A., Stewart, R. B., Perlanski E.: Salt Restriction and the Voluntary Intake of Ethanol in Rats. Physiol Pyschol 12:242-246, 1984.

Grupp, L. A., Stewart, R. B., Perlanski, E.: Dietary Salt and Doca Salt Treatments Modify Ethanol Self-Selection in Rats. Behav Neural Biol 40:239-250, 1984.

Grupp, L. A., Stewart, R. B., Perlanski, E.: Diet and Diuretics in the Reduction of Voluntary Alcohol Drinking in Rats. Alcohol and Alcoholism 21: 75-79, 1986.

Grupp, L. A., Perlanski, E., Wanless, I. R., Stewart, R. B.: Voluntary Alcohol Intake in the Hypertensive Prone Dahl Rat. Pharmacol Biochem Behav 24:1167-1174, 1986.

Grupp, L. A., Perlanski, E., Leenen, F. H. H., Stewart, R. B.: Renal Artery Stenosis: An Example of How the Periphery Can Modulate Voluntary Alcohol Drinking. Life Sci 40:563-570, 1987.

LeBlanc, A. E.: Microdetermination of Alcohol in Blood by Gas-Liquid Chromatography, Can J. Physiol Pharmacol 46:665-667, 1968.

Linseman, M.: Alcohol Consumption in Free-Feeding Rats-Procedural Genetic and Pharmacokinetic Factors. Psychopharmacology 92:254-261, 1987.

Ashley, M. J., Rankin, J. G.: Alcohol Consumption and Hypertension: The Evidence from Hazardous Drinking Alcohol Populations. Austr New Zealand J Med. 9:201-206, 1979.

Klatsky, A. L., Freedman, G. D., Seigelaub, A. B., Gerard, M. J.: Alcohol Consumption and Blood Pressure. New Engl J Med 296:1194-1200, 1977.

Goldblatt, H., Lynch, J., Hanzal, R. F., Summerville, W. W.: Studies on Experimental Hypertension. I. The Production of Persistent Elevation of the Systolic Blood Pressure by Means of Renal Ischemia. J Exp Med 59:347-360, 1934.

Leenen, F. H. H., Myers, M. G.: Pressor Mechanisms in Renovascular Hypertensive Rats, in de Jong W (ed): Handbook of Hypertension: Experimental and Genetic Models of Hypertension, vol. 4, Amsterdam, Elsevier, 1971, p. 24.

Schiffrin, E. L., Gutkowska, J., Genest J.: Mechanism of Captopril Induced Renin Release. Proc Soc Exp Biol Med 167:327-332, 1981.

(List continued on next page.)

*Primary Examiner*—A. Lionel Clingman
*Assistant Examiner*—Erin M. Higgins
*Attorney, Agent, or Firm*—Weingarten, Schurgin, Gagnebin & Hayes

[57] ABSTRACT

A method is provided for treating warm-blooded animals so as to reduce their voluntary alcohol consumption comprising the administration to the animals of an angiotensin converting enzyme inhibitor.

5 Claims, 6 Drawing Sheets

OTHER PUBLICATIONS

Schiffrin, E. L., Gutkowska, J., Thibault, G., Genest, J.: Effect of Enalapril (MK-421), An Orally Active Angiotensin I Converting Enzyme Inhibitor, on Blood Pressure, Active and Inactive Plasma Renin, Urinary Prostaglandin $E_2$ and Kallikrein Excretion in Conscious Rats. Can J Physiol Pharmacol 62:116–123, 1984.

Gill, K., France, C., Amit, Z.: Voluntary Ethanol Consumption in Rats: An Examination of Blood/Brain Ethanol Levels and Behavior. Alcoholism: Clin Exp Res 10:457–462, 1986.

Meshcheryakov, A. F. et al., Chem. Abstracts 104:83598r (1986) in: Fiziol. Zh. SSSR im. I. M. Sechenova 71(12):1546–52 (1985).

REDUCTION OF VOLUNTARY ALCOHOL CONSUMPTION BY TREATMENT WITH ANGIOTENSIN CONVERTING ENZYME INHIBITORS

FIELD OF THE INVENTION

The present invention relates to a new method of treatment to reduce voluntary alcohol intake in warm-blooded animals.

BACKGROUND OF THE INVENTION

Although alcohol abuse is a serious problem in our society, effective treatments for reducing voluntary alcohol consumption are lacking.

One commonly used treatment is the administration of an alcohol-sensitizing drug, of which disulfiram (Antabuse: trade mark of Ayerst) is probably the best known. Such drugs do not reduce alcohol intake by interference with the biological mechanisms involved in alcohol intake, but rather induce an aversive reaction to consumed alcohol in the subject, so as to deter further drinking. Such treatment is unpleasant for the subject should alcohol be consumed, patient compliance is poor and evidence of the treatment's effectiveness is weak.

Another approach has been the use of agents which alter neurochemical activity, for example the administration of antidepressants such as lithium.

Indications that brain serotonin levels may be low in alcoholics have led to treatment with drugs which are serotonin uptake inhibitors, such as zimelidine and citalopram.

None of these treatments has proved particularly effective.

Recent studies by the inventors have shown that various manipulations which are known to affect the renin-angiotensin system, such as restriction of salt intake and administration of diuretics, also modulate voluntary alcohol consumption in rats.

One class of agents which affect the renin-angiotensin system is the angiotensin converting enzyme (ACE) inhibitors which prevent conversion of angiotensin I to angiotensin II. These agents are known to be useful in the treatment of hypertension and such use has shown them to be safe and without significant side-effects.

SUMMARY OF THE INVENTION

The present invention provides a method of treating warm-blooded animals so as to reduce their voluntary alcohol consumption which comprises administering an angiotensin converting enzyme inhibitor to the animals.

In accordance with the present invention, administration of angiotensin converting enzyme inhibitors such as captopril or enalapril to rats reduced their voluntary alcohol consumption specifically, across a wide spectrum of conditions and without deleterious side effects.

DESCRIPTION OF DRAWINGS

The method of treatment in accordance with the present invention will now be described by way of example and with reference to the drawings in which.

DESCRIPTION OF THE INVENTION

EXAMPLE 1

Figure 1A:
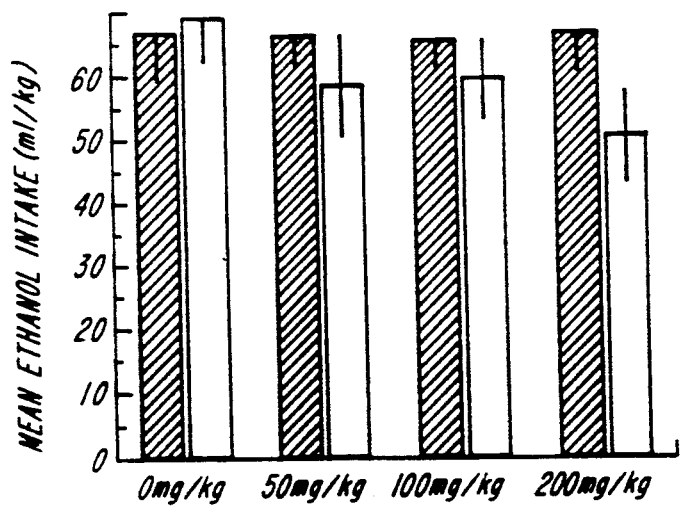
FIG. 1A and 1B are bar diagrams showing, in FIG. 1A, mean 24-hr. alcohol intake and in FIG. 1B, mean 24-hr. water intake of rats over two time periods, phase 1 (solid bars) and phase 2 (open bars).

Treatment of rats with captopril (Capoten) under conditions of free access to alcohol.

Subjects. Thirty-six naive male Wistar rats (Charles River, Montreal) were used, weighing between 254 and 327 g at the beginning of the study. The animals were individually housed in cages equipped with a glass feeder cup containing Purina Rat Chow and two graduated drinking tubes spaced 15 cm apart. A reversed 12 hr/12 hr light/dark cycle was in effect throughout.

Procedure. All animals were allowed free access to the two drinking tubes, one containing 4% alcohol (ethanol, w/v) made up in tap water and the other containing only tap water. The positions of the two tubes were alternated daily and fluid consumption was measured over consecutive 24 hr. periods.

The study was divided into two phases. During Phase 1 (14 days) all rats were injected with 0.9% saline intraperitoneally (i.p) twice per day, once in the morning and again in the early afternoon. At the end of this phase, the rats were divided equally into four groups for alcohol consumption. In phase 2 (19 days) three of the four groups received doses of 25, 50 or 100 mg/kg captopril, respectively, in each of the two daily injections. The fourth group continued to receive 0.9% saline. Captopril was prepared in 0.9% saline and injected in concentrations adjusted so that the various doses were all administered in a volume of 1 ml/100 g body weight.

At the end of the study, five rats from each group were injected i.p. with a dose of 2.5 g/kg alcohol [12.5% (w/v)]. Blood samples were taken from the cut tip of the tail at intervals of 15 min. during the first hour after the injection and thereafter at hourly intervals for the next four hours. These blood samples were prepared and analyzed by gas-liquid chromatography according to the method of LeBlanc, (Canadian Journal of Physiology and Pharmacology, (1968), v. 46, p. 665) and were used to examine the effect of captopril treatment on the pharmacokinetics of alcohol.

Figure 1B:
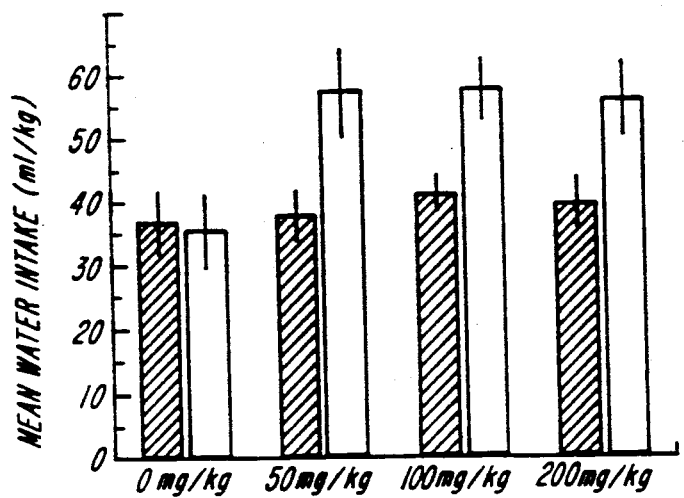

FIG. 1 shows the means 24-hr. alcohol intake (panel a) and water intake (panel b) over phase 1 (solid bars) and phase 2 (open bars) for the group treated with saline only (0 mg/kg) and the three groups treated with captopril at the indicated doses.

A two way analysis of variance of the 24-hr. alcohol intake data in the three captopril-treated groups of Example 1 (FIG. 1a) revealed a non-significant effect of Dose [$F(2,24) = 0.10$, n.s.], a significant effect of Phase [$F(1,24) = 11.60$, $p < 0.002$] and a non-significant Dose×Phase interaction [$F(2,34) = 1.03$, n.s.]. Analysis showed that captopril treatment in phase 2 significantly decreased alcohol intake compared to control drinking in phase 1 ($T_{26} = 3.40$, $p < 0.01$). This decrease, hoever, was not dose dependent. The saline group (0 mg/kg, FIG. 1a) as expected did not alter its alcohol intake across the two phases ($T_8 0.54$, n.s.). These results indicate that captopril treatment can attenuate voluntary alcohol intake.

A two-way analysis of variance of the 24 hr. water intake data in the three captopril-treated groups of Example 1 (FIG. 1b) showed a non-significant effect of Dose [$F(2,24) = 0.05$, n.s.], a significant effect of Phase [$F(1,24) = 25.68$, $p < 0.02$] and a non-significant Dose×Phase interaction [$F(2,24) = 0.10$, n.s.]. Analysis showed that captopril treatment significantly increased water intake in phase 2 compared to control drinking in phase 1 ($T_{26} = -5.25$, $p < 0.01$). Again, this effect was not dose dependent. Water intake in the saline group (FIG. 1b) did not change ($T_8 = 0.45$, n.s). These results indicate that captopril treatment can also increase water intake.

Figure 2:
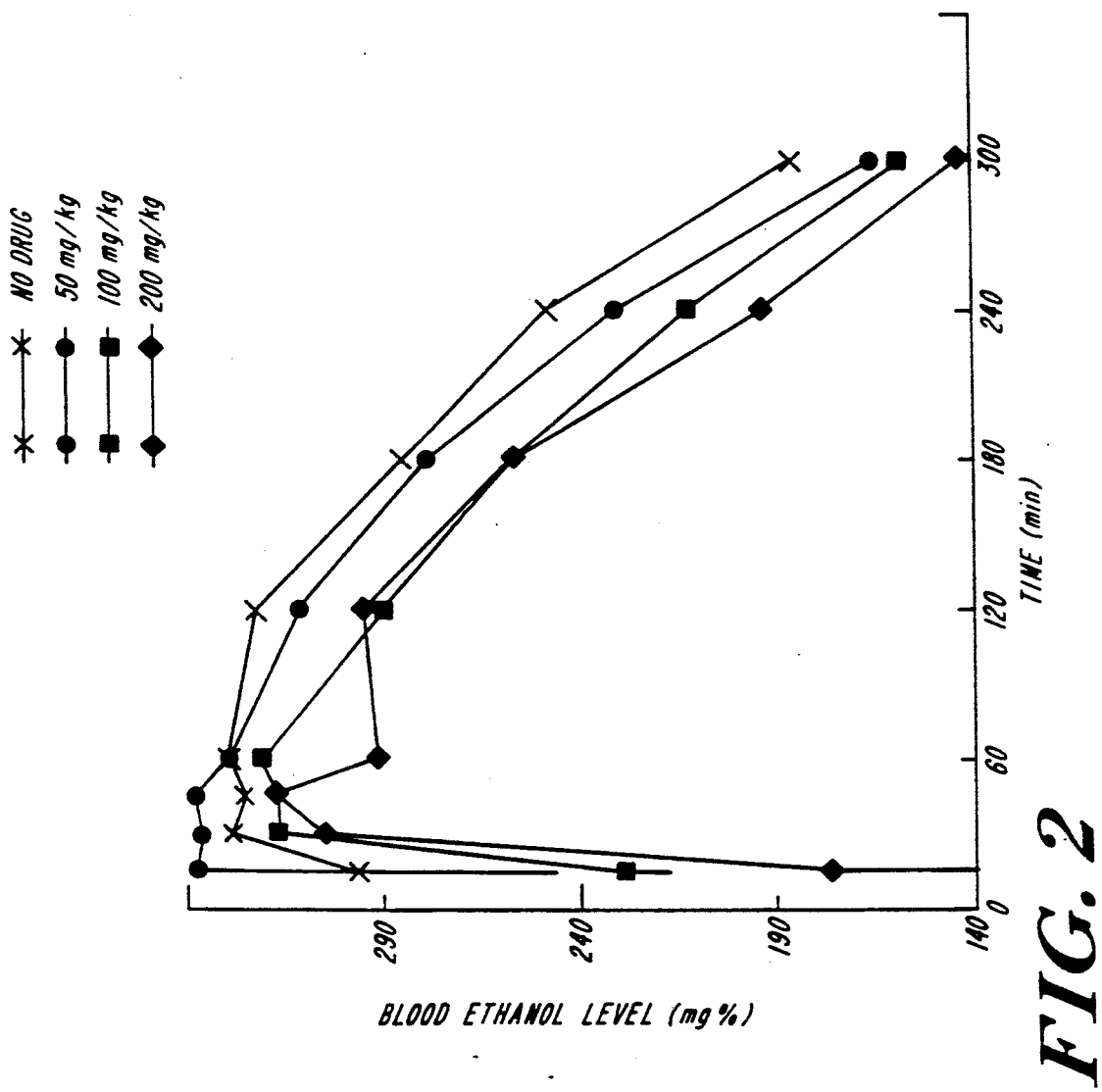
FIG. 2 is a graph showing blood alcohol levels (mg %) of the four treatment groups measured at various times (min) after an initial dose of 2.5 g/kg alcohol injected i.p. at time zero. Vertical lines represent the standard error of the mean.

FIG. 2 shows the mean blood alcohol levels for the four groups of rats in Example 1 at the eight sampling times. The last four points on the descending portion of the curves were used to calculate the slopes. These slopes of the linear portion of the curves represent the rate of alcohol metabolism. A one way analysis of variance of the rates of alcohol metabolism showed a non-significant effect of Group [$F(3,16) = 0.93$, n.s.] indicating that captopril treatment did not change the rate of alcohol metabolism. Extension of the linear portions of the curves back to the ordinate allowed for the determination of concentrations at time zero in each rat in the respective groups. These values were used to calculate the volumes of distribution. A one-way analysis of variance of the volume of distribution data showed a non-significant effect of Group [$F(3,16) = 2.25$, n.s.] indicating that captopril treatment also did not change the volume of distribution. A two-way analysis of variance of the blood alcohol levels measured at the first three time intervals following the alcohol injections (i.e. 15, 30 and 45 min) showed a non-significant effect of Group [$F(3,16) = 2.62$, n.s.], a significant effect of Interval [$F(2,32) = 15.06$, $p < 0.01$] and a significant Group×Interval interaction [$F(6,32) = 3.48$, $p < 0.01$]. The significant Group×Interval interaction indicates that the two higher doses of captopril slowed the absorption of alcohol but only during the first 15 min. following the injection.

Example 1 demonstrated that captopril can reduce the voluntary intake of alcohol and that this effect is not due to a change in the distribution or metabolism of alcohol. Since alcohol was self-administered orally by the animals but given by injection to study the pharmacokinetics, the slower alcohol absorption in the groups treated with captopril may not be an accurate reflection of absorption from the stomach after oral intake. Furthermore, the difference in absorption between the captopril and vehicle treated groups could account for the difference in intake only if alcohol intake varied directly with rate of absorption. However, it has been suggested that alcohol intake varies inversely, not directly With rate of absorption.

Since water intake was not likewise depressed, but in fact enhanced by captopril, the attenuation appears to be specific to alcohol rather than a generalized effect on all available fluids. Furthermore, since water intake increased following captopril treatment, it appears that the animals were healthy and attempting to maintain a normal fluid balance. The vehicle injected group did not show changes in either alcohol or water intake, indicating that injections per se did not alter fluid intake and also that the pattern of alcohol intake did not change over the course of the study.

EXAMPLE 2

Since there is a correlation between alcohol consumption and hypertension in humans, it was of interest to examine the effect of captopril on alcohol intake in hypertensive animals. Accordingly, the effect of captopril on alcohol intake was examined in animals rendered hypertensive by the Two-Kidney, One-Clip (T-K,O-C) model of hypertension described by Goldblatt et al., (1934), Journal of Experimental Medicine, v. 59, p. 347. In this model, one renal artery is constricted (renal artery stenosis) while the contralateral kidney is untouched. Renin-angiotensin activity becomes elevated two to three weeks following this procedure and remains elevated thereafter for several months.

Subjects. Twenty-seven naive male Wistar rats (140–160 g) were used. All feeding and housing conditions were the same as in Example 1.

Procedure. The animals were anaesthetized with a mixture of halothane and oxygen and either had a 0.2 mm solid silver clip applied to the left renal artery (hypertensive group, n=11) or underwent a sham procedure including all surgery but no clip (normotensive group, n=16). The right kidney was left untouched. Three weeks following the operation, when both blood pressure (BP) and plasma renin activity (PRA) are elevated in the clipped animals, systolic BP was measured in both groups.

Animals were then offered free access to both alcohol (4%, w/v) and water. The positions of the two tubes were alternated daily and consumption was measured over consecutive 24 hr. periods. After the first 12 days, each animal received one 2.5 g/kg intraperitoneal (i.p.) injection of alcohol in order to establish an alcohol disappearance curve. For the next eleven days, animals were again offered free access to alcohol and water and then both groups received captopril injections i.p. twice daily in a dose of 50 mg/kg/injection for 11 days and then in a dose of 100 mg/kg/injection for a further 11 days. Blood pressure was again measured at the end of the study.

Figure 3A:
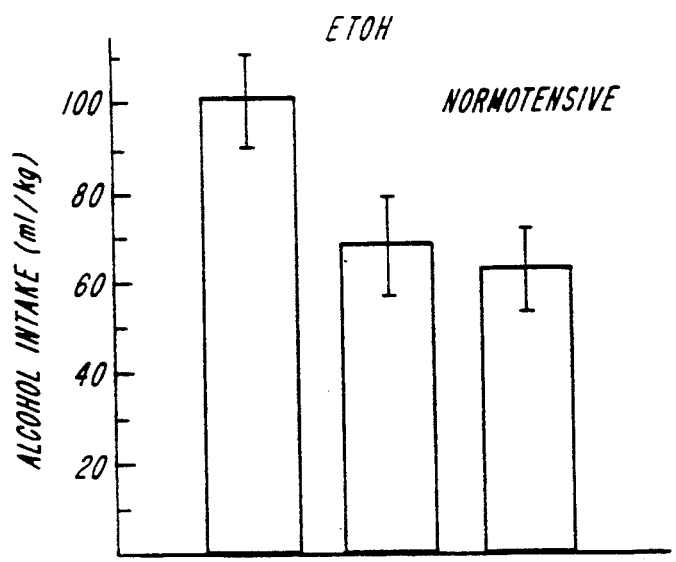
FIG. 3A and FIG. 3b are bar diagrams showing mean 24-hr. alcohol intake (ml/kg) before (baseline) and after captopril treatment in normotensive (FIG. 3A) and hypertensive (FIG. 3B) rats. Vertical lines represent standard error of the mean.
Figure 3B:
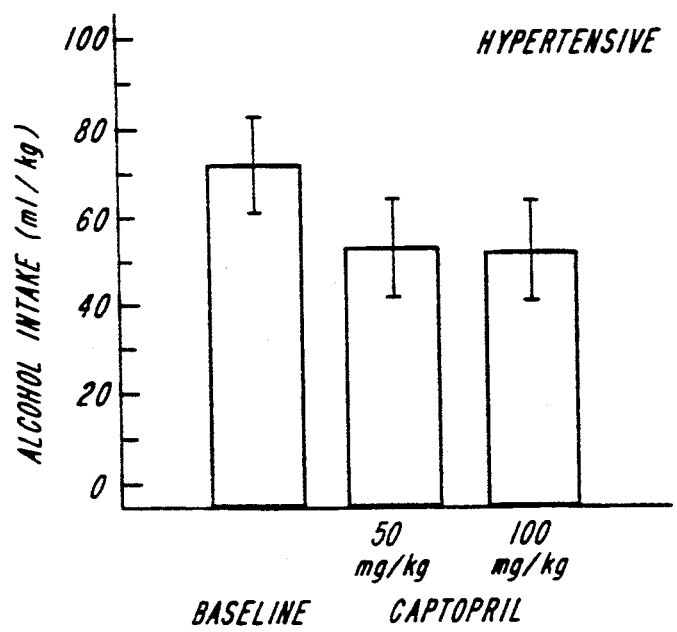

FIG. 3 illustrates the effect of the two doses of captopril on alcohol drinking in the normotensive and hypertensive groups of Example 2. FIG. 3A shows that captopril significantly reduced voluntary alcohol intake in the normotensive group $F(2,30) = 25.3$, $p < 0.001$] and both the 50 mg/kg ($T_{15} = 4.4$, $p < 0.01$) and the 100 mg/kg doses ($T_{15} = 7.2$, $p < 0.01$) were effective. FIG. 3B shows that captopril also attenuated alcohol intake in the hypertensive group, although the reduction did not reach statistical significance [$F(2,20) = 1.8$, n.s.].

Figure 4A:
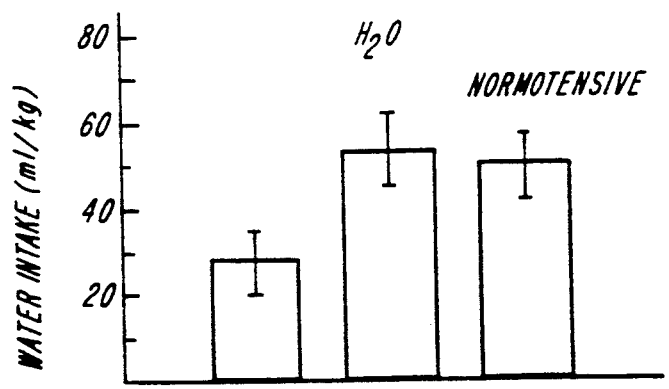
FIG. 4A and 4B are bar diagrams showing mean 24-hr. water intake (ml/kg) before (baseline) and after captopril treatment in normotensive (FIG. 4A) and hypertensive (FIG. 4B) rats. Vertical lines represent standard error of the mean.
Figure 4B:
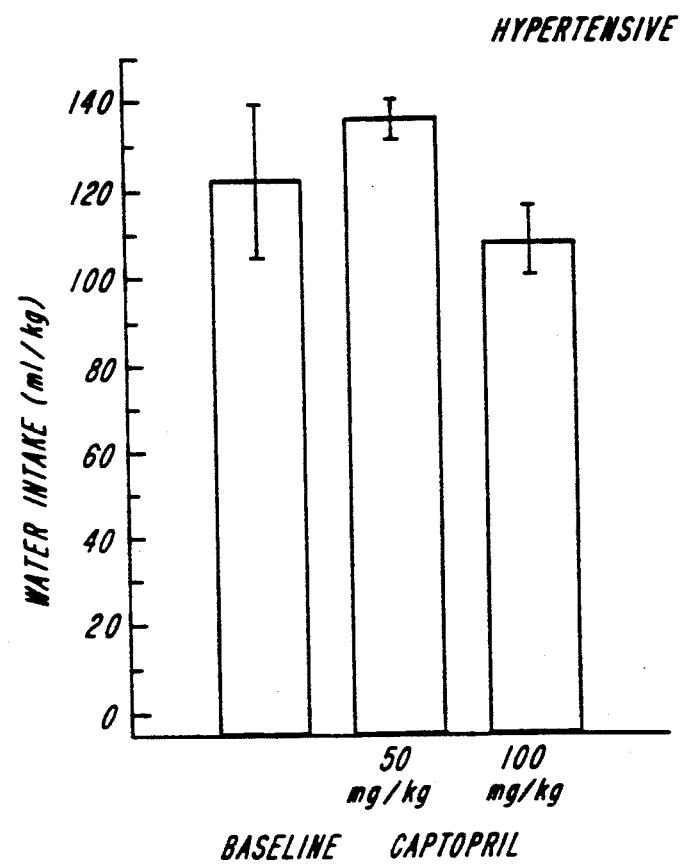

FIG. 4 illustrates the group changes in water intake FIG. 4A shows that the normotensive group increased its intake during the captopril administration [$F(2,30) = 16.3$, $p < 0.01$] and that both doses were effective in this regard when compared to baseline levels of consumption ($T_{15} = 4.2$, $p < 0.01$-50 mg/kg; $T_{15} = 5.0$, $p < 0.01$-100 mg/kg). However, in the hypertensive group (FIG. 4B), water consumption was not significantly altered by the captopril administration [$F(2,20) = 1.97$, n.s.].

Figure 5:
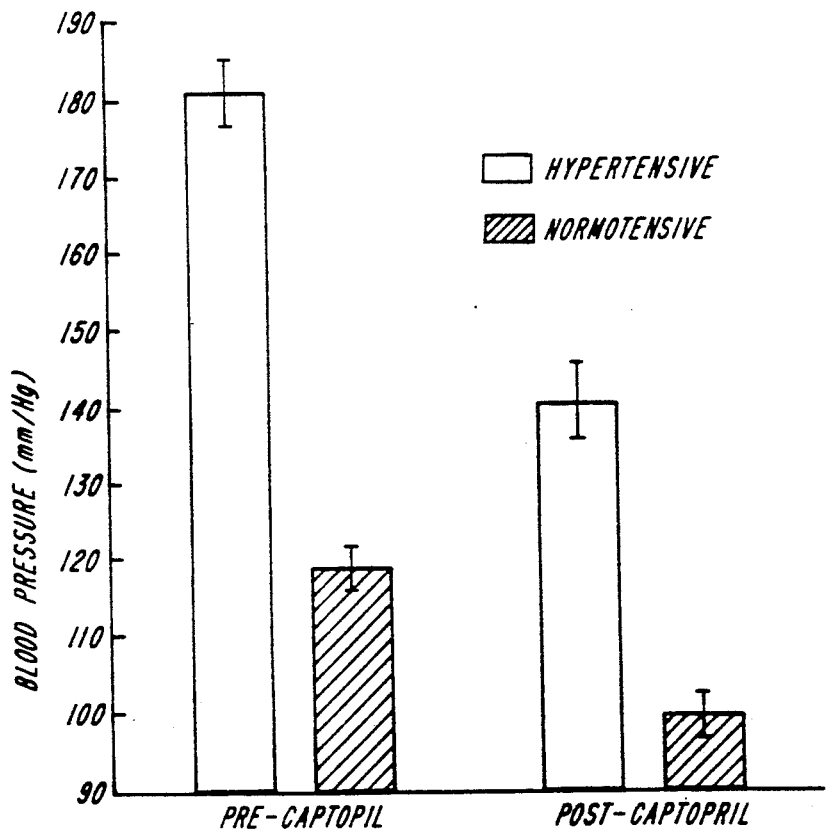
FIG. 5 is a bar diagram showing mean blood pressure in normotensive and hypertensive rats before and after captopril treatment. Vertical lines represent standard error of the mean.

FIG. 5 illustrates the mean blood pressure in both groups of animals of Example 2 before and after captopril administration. Captropril significantly lowered blood pressure in both the hypertensive ($T_{15} = 4.57$, $p < 0.01$) and the normotensive groups ($T_{10} = 5.2$, $p < 0.01$).

The results of Example 2 confirm the findings of Example 1, in that captopril administration significantly attenuated voluntary alcohol drinking in normotensive animals. Although there was a tendency for all doses to reduce intake in Example 1, only the 200 mg/kg dose significantly attenuated intake. In Example 2, a significant reduction in alcohol intake was also achieved at a lower daily captopril dose (i.e., 100 mg/kg), suggesting that very high doses of captopril may be unnecessary to reduce alcohol intake. While effective in the normotensive animals, captopril did not significantly reduce alcohol intake in the hypertensive group although there was a clear tendency in that direction. The increase in water intake in the normotensive group also replicates the findings of Example 1. The failure of the hypertensive group to show a similar increase in water intake may reflect a ceiling effect in that water intake was already enhanced as a consequence of the elevated plasma renin levels.

EXAMPLE 3

In Examples 1 and 2, doses of converting enzyme inhibitor were used which are known to elevate plasma renin activity (PRA) (Schiffrin et al., (1981), Proc. Soc. Exp. Biol. Med., v. 167, p. 327): and which reduced blood pressure (BP). These doses were large (i.e. 50 to 100 mg/kg b.i.d.) yet effective in reducing alcohol intake. Schiffrin et al. (Canadian J. Physiol. Pharmacol., (1984), v. 62, p. 116) have established that 1 mg/kg of enalapril (Vasotec), another angiotensin converting enzyme inhibitor, does not elevate PRA or reduce BP in T-K,O-C hypertensive rats.

The third example shows the effect of this dose of enalapril on voluntary alcohol drinking. Because this is a rather low dose of the drug, it was important that alcohol intake occur in close temporal proximity to the administration of enalapril. We therefore used a limited access procedure which makes alcohol available for only 1 hr. per day. With this procedure most animals rapidly consume alcohol in quantities which produced detectable blood alcohol levels.

Subjects. The subjects were 32 naive male Wistar rats weighing 140 to 160 g. at the beginning of the study. They were individually housed in cages equipped with water and food and kept on a reversed 12 hr/12 hr light/dark cycle with lights off at 7:00 a.m.

Procedure

Surgery. All animals underwent renal artery clipping as described in Example 2. Three weeks following the operation when both BP and PRA are known to be elevated, systolic BP was measured by the tail cuff method.

Alcohol drinking. The animals were divided into two groups, equated for BP, designated to be pretreated with either enalapril 1 mg/kg or saline vehicle. Every day, each animal was removed from its home cage and placed for 1 hr. in a "drinking" cage which had two graduated drinking tubes, one containing alcohol 3% (w/v) and the other water. The position of the two fluids was alternated daily and no food was available during this one hour period. After one hour had elapsed, the amounts of each fluid consumed were recorded and the animals returned to their home cages. One hour prior to placing the animals in the drinking cages, each animal received its respective i.p. injection of either enalapril (1 mg/kg) or saline.

At the conclusion of the study, BP was again measured in both groups.

Figure 6:
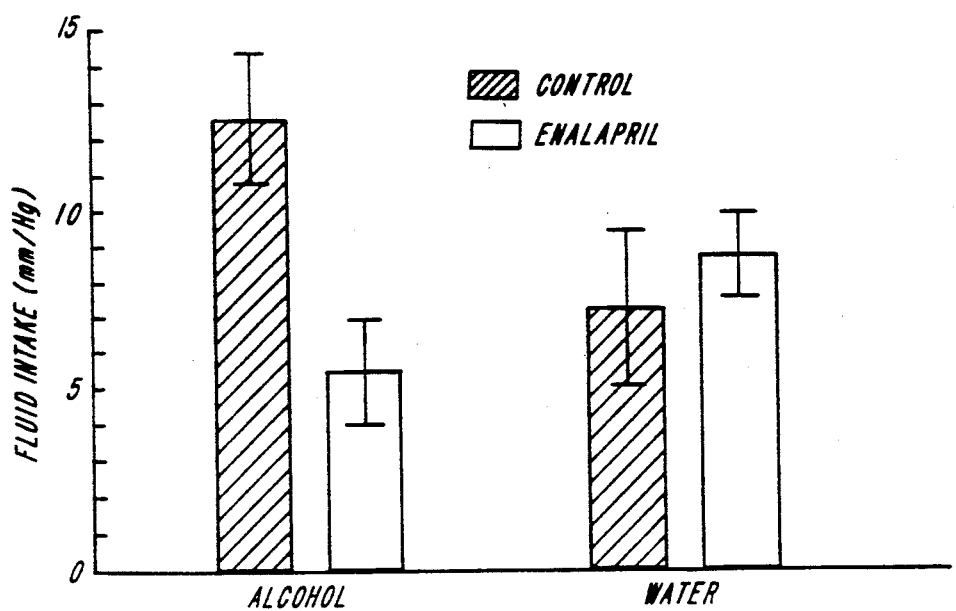
FIG. 6 is a bar diagram showing mean alcohol and water intake during a one hour period of access to alcohol. All animals were hypertensive; one group (open blocks) received i.p. injections of enalapril (1 mg/kg), the other group (shaded blocks) received injections of the vehicle (saline). Vertical lines represent the standard error of the mean.

FIG. 6 illustrates the alcohol intake for both groups averaged across the 14 days' study of Example 3. The T-K, O-C group pretreated with enalapril drank significantly less alcohol than the T-K, O-C group pretreated with the vehicle ($T_{30} = 3.04$, $p < 0.002$). Since 1 mg/kg enalapril has been found not to alter PRA, the present finding suggests that the ability of enalapril to reduce alcohol intake may not be dependent on a change in PRA.

Figure 7:
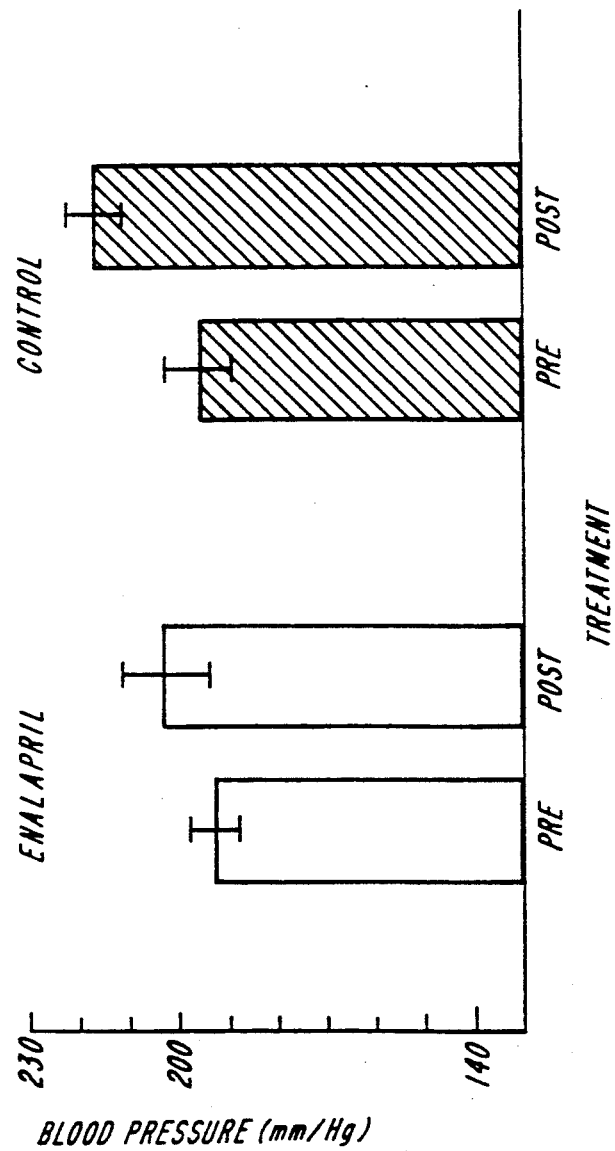
FIG. 7 is a bar diagram showing mean blood pressure in enalapril-treated and control (saline-treated) rats before and after drug treatment. All animals were rendered hypertensive by renal artery constriction. Vertical lines represent standard error of the mean.

FIG. 7 illustrates the average blood pressure for both groups of animals before and after pretreatment with enalapril or vehicle. As expected, the blood pressure of both groups was elevated following the T-K, O-C procedure (normal Wistar rate blood pressure 100–120 mm Hg.). Pretreatment with 1 mg/kg of enalapril daily for 14 days failed to reduce blood pressure ($T_{17} = 1.02$, n.s) although blood pressure in the group receiving saline continued to rise ($T_{13} = 3.08$, $p < 0.5$). This finding is in agreement with Schiffrin et al. who also did not find a reduction in blood pressure in T-K, O-C rats even after twice daily treatment with 1 mg/kg of enalapril. These findings suggest that the ability of enalapril to reduce alcohol intake is not dependent upon a concurrent reduction in blood pressure.

FIG. 6 also shows the average water intake for both groups of rats in Example 3. Water intake was not significantly elevated in the T-K, O-C rats receiving enalapril. This confirms the suggestion that the 1 mg/kg dose of enalapril did not elevate PRA because the enhanced water intake sometimes associated with the administration of converting enzyme inhibitors is related to an elevated PRA. Furthermore, this finding demonstrates that the ability of enalapril to reduce alcohol intake does not depend on a concurrent change in the intake of water. This indicates that the 1 mg/kg dose of enalapril was specific in its ability to reduce voluntary alcohol drinking.

From the foregoing, it will be noted that ACE inhibitors, captopril and enalapril when administered to rats, in a dose in the range of 1 to 200 mg/kg body weight/day produce a reduction of voluntary alcohol consumption.

It will also be noted that ACE inhibitors reduce voluntary alcohol consumption in rats whether alcohol is continuously available (when the animals typically drink in a number of short bouts distributed throughout the day) or is available only for one hour per day (when the animals typically drink in one or two extended bouts and consume in excess of their ability to metabolize alcohol).

Furthermore, reduction of alcohol consumption was achieved in both normotensive and hypertensive animals. As shown by Example 2, captopril administration reduced blood pressure and alcohol consumption simultaneously. Since a significant number of alcoholics and heavy drinkers are hypertensive, the possibility arises of treating both conditions with the same medication.

From the foregoing, it will be seen that an effective method of treatment without harmful side-effects has been provided whereby the voluntary alcohol consumption of warm blooded animals is reduced under a wide variety of conditions.

What is claimed:

1. A method for the treatment of alcoholism comprising administering to warm-blooded animals in need of such treatment a therapeutically effective amount of an angiotensin converting enzyme inhibitor selected from the group consisting of captopril and enalapril.

2. A method for treatment of alcoholism comprising administering to warm-blooded animals in need of such treatment a therapeutically effective amount of an angiotensin converting enzyme inhibitor selected from the group consisting of captopril and enalapril and a pharmaceutically acceptable carrier.

3. A method of treating warm-blooded animals so as to reduce their voluntary alcohol consumption which comprises administering to said warm-blooded animals in need of such treatment captopril in a does of 50 to 200 mg/kg body weight/day.

4. A method of treating warm-blooded animals so as to reduce their voluntary alcohol consumption which comprises administering to said animals in need of such treatment enalapril in a dose of approximately 1mg/kg body weight/day.

5. A method of treating warm-blooded animals so as to reduce their voluntary alcohol consumption which comprises administering to said animals in need of such treatment captopril in a dose of approximately 1 mg/kg body weight/day.

* * * * *